(12) United States Patent
McCracken et al.

(10) Patent No.: US 6,437,082 B1
(45) Date of Patent: Aug. 20, 2002

(54) INFRARED EVALUATION OF THE STOICHIOMETRIC RATIO OF DIHYDRIC PHENOL TO DIARYLCARBONATE DURING PRODUCTION OF POLYCARBONATES

(75) Inventors: Linda McCracken; Patrick McCloskey, both of Schenectady, NY (US); Eva Mardomingo-Santás, Cartagena (ES); Timothy Brydon Burnell, Schenectady, NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/603,488

(22) Filed: Jun. 23, 2000

(51) Int. Cl.⁷ ............................................... C08G 64/03
(52) U.S. Cl. ...................................... 528/196; 528/198
(58) Field of Search .................................. 528/196, 198

(56) References Cited

U.S. PATENT DOCUMENTS 5,114,861 A * 5/1992 Silva et al. ................... 436/85

FOREIGN PATENT DOCUMENTS

EP         0 601 602 A2    6/1994
WO         WO 96/10009     4/1996

OTHER PUBLICATIONS

Pat. Abst. of Japan 02306936 Kao Corp. Dec. 20, 1990.

* cited by examiner

Primary Examiner—Terressa M. Boykin
(74) Attorney, Agent, or Firm—Oppedahl & Larson LLP (57) ABSTRACT

The stoichiometric ratio of dihydric phenol to diarylcarbonate during production of polycarbonates can be evaluated by infrared analysis, preferably using an FTIR spectrometer, to detect the amount of BPA or other dihydric phenol in the mix tank. In one format of the method, one or both of two characteristic peaks, reflecting the methyl CH bonds and hydroxyl OH bonds are evaluated. These peaks occur equally in BPA monomers and oligomers, and hence are independent of the degree of oligomerization or polymerization which has occurred. For this reason, monitoring of stoichiometry can be performed on the contents of the mix tank, or on the products from or contents of any downstream reactors. Using a calibration curve, the absorbance associated with these bonds is converted into a measure of the concentration of BPA and from that to first moles and then grams of BPA in the mixture being tested. The amount of DPC is determined by subtracting the number of grams of BPA from the total initial sample weight. In another format, a ratio of the size of the peaks associated with DPC carbonyl and BPA methyl is used directly to determine the ratio of DPC to BPA.

20 Claims, 6 Drawing Sheets

INFRARED EVALUATION OF THE STOICHIOMETRIC RATIO OF DIHYDRIC PHENOL TO DIARYLCARBONATE DURING PRODUCTION OF POLYCARBONATES

BACKGROUND OF THE INVENTION

This application relates to an improved method for the production of polycarbonates.

Polycarbonates are conventionally produced by the reaction of a dihydric phenol, such as bisphenol A (BPA), and a diarylcarbonate, such as diphenyl carbonate (DPC). BPA and DPC are combined together is a monomer mixing tank, and the resulting mixture is fed into the reactor to produce the polycarbonate. The characteristics of the product polycarbonate is determined in part by the relative amounts of BPA and DPC in the monomer mix tank. This arises from a relationship between the end-cap level (i.e., the termination of a polymer in a manner unsuitable for further chain extension) and monomer ratio.

This relationship between product characteristics and monomer ratio makes it desirable to test the levels of BPA and DPC in the mix tank. At present, this is done using an HPLC analysis. The efficacy of the HPLC analysis is limited, however, because in some instances, catalyst is added to form an equilibrated oligomer-containing mixture in the mix tank. When HPLC is used to analyze such mixtures, the measured ratio determined by HPLC provides an inaccurate measure of the actual ratio of BPA to DPC. Thus, when an equilibrated mixture is formed, HPLC fails to accurately predict the characteristics of the final product, and cannot provide a reliable guide to adjustment of the amounts of materials added to the monomer mix tank. Some alternative form of monitoring is therefore required for use in such systems.

SUMMARY OF THE INVENTION

The present invention provides a new method for evaluating the stoichiometric ratio of dihydric phenol to diarylcarbonate during production of polycarbonates which does not suffer from the deficiencies of the HPLC technique. In accordance with this method, infrared analysis, preferably using an FTIR spectrometer, is utilized to detect the amount of BPA or other dihydric phenol in the mix tank. In one embodiment of the invention, one or both of two characteristic peaks, reflecting the methyl CH bonds and hydroxyl OH bonds are evaluated. These peaks occur equally in BPA monomers and oligomers, and hence are independent of the degree of oligomerization or polymerization which has occurred. For this reason, monitoring of stoichiometry can be performed on the contents of the mix tank, or on the products from or contents of any downstream reactors. Using a calibration curve, the absorbance associated with these bonds is converted into a measure of the concentration of BPA and from that to first moles and then grams of BPA in the mixture being tested. The amount of DPC is determined by subtracting the number of grams of BPA from the total initial sample weight. In another embodiment of the invention, a ratio of the size of the peaks associated with DPC carbonyl and BPA methyl is used directly to determine the ratio of DPC to BPA.

DETAILED DESCRIPTION OF THE INVENTION

In known phosgene-free processes for making polycarbonate, a dihydric phenol and a diarylcarbonate are reacted in the presence of a basic catalyst. In the commercial manufacture of polycarbonate, the most commonly employed dihydric phenol is BPA, and the most commonly employed diarylcarbonate is DPC. However, in the discussion below, BPA and DPC are only non-limiting examples. There are other dihydric phenols and diarylcarbonates which are known for the formation of the polycarbonates, and the present invention can be used with streams of these materials as well. Examples of such materials include but are not limited to:

as the dialkyl carbonate: dimethyl carbonate, diethyl carbonate, dipropyl carbonate, diallyl carbonate, dibutenyl carbonate, dibutyl carbonate, dipentyl carbonate, dihexyl carbonate, diheptyl carbonate, dioctyl carbonate, dinonyl carbonate, didecyl carbonate, dicyclopentyl carbonate, dicyclohexyl carbonate, dicycloheptyl carbonate, dibenzyl carbonate, diphenyl carbonate, di(phenylpropyl) carbonate, di(phenylbutyl) carbonate, di(chlorobenzyl) carbonate, di(methoxybenzyl) carbonate, di(methoxymethyl) carbonate, di(methoxyethyl) carbonate, di(chloroethyl) carbonate and di(cyanoethyl) carbonate, including the various isomers thereof;

as the dihydric phenol: bis(4-hydroxyphenyl)methane, 1,1-bis(4-hydroxyphenyl)ethane, 2,2-bis(4-hydroxyphenyl) propane, 2,2-bis(4-hydroxyphenyl)butane, 2,2-bis-(4-hydroxyphenyl)octane, bis(4-hydroxyphenyl) phenylmethane, 2,2-bis(4-hydroxy-1-methylphenyl) propane, 1,1-bis(4-hydroxy-tert-butylphenyl)propane, 2,2-bis(4-hydroxy-3-bromophenyl)propane, and other bis (hydroxyaryl) alkanes; 1,1-bis(4-hydroxyphenyl) cyclopentane, 1,1-bis(4-hydroxyphenyl)cyclohexane, and other bis(hydroxyaryl)cycloalkanes; 4,4'-dihydroxydiphenyl ether, 4,4'-dihydroxy-3,3'-dimethylphenyl ether, and other dihydroxyaryl ethers; 4,4'-dihydroxydiphenyl sulfide, 4,4'-dihydroxy-3,3'-dimethylphenyl sulfide, and other dihydroxydiaryl sulfides; 4,4'-dihydroxydiphenyl sulfoxide, 4,4'-dihydroxy-3,3'-dimethyldiphenyl sulfoxide, and other dihydroxydiaryl sulfoxides; and 4,4'-dihydroxydiphenyl sulfone, 4,4'-dihydroxy-3,3'-dimethyldiphenyl sulfone, and other dihydroxydiaryl sulfones, resorcin, 3-methylresorcin, 3-ethylresorcin, 3-propylresorcin, 3-butylresorcin, 3-tert-butylresorcin, 3-phenylresorcin, 3-cumylresorcin, 2,3,4,6-tetrafluororesorcin, 2,3,4,6-tetrabromoresorcin, and other substituted resorcins; catechol; hydroquinone, 3-methylhydroquinone, 3-methylhydroquinone, 3-propylhydroquinone, 3-butylhydroquinone, 3-tertbutylhydroquinone, 3-phenyl-hydroquinone, 3-cumylhydroquinone, 2,3,5,6-tetramethylhydroquinone, 2,3,5,6-tetra-tertrabutylhydroquinone, 2,3,5,6-tetrafluorohydroquinone, 2,3,5,6-tetrabromohydroquinone, and other substituted hydroquinones.

To control the characteristics of the product polycarbonate, and in particular those characteristics such as molecular weight and viscosity which are related to end-cap level, the relative amounts of dihydric phenol and diarylcarbonate are controlled. Since end-capping can occur through the reaction of phenol in place of the dihydric phenol, and since phenol is a reaction by-product of the polymerization process, lower ratios of dihydric phenol to diarylcarbonate favor increased end-cap levels and shorter polymers. Conversely, higher ratios of dihydric phenol to diarylcarbonate favor decreased end-cap levels and longer polymers. Thus, for any given manufacturing process, one can define a range of dihydric phenol and diarylcarbonate levels which will result in the desired end-cap level. As used in the specification and claims hereof, this range is referred to as a "pre-defined range"

Figure 1:
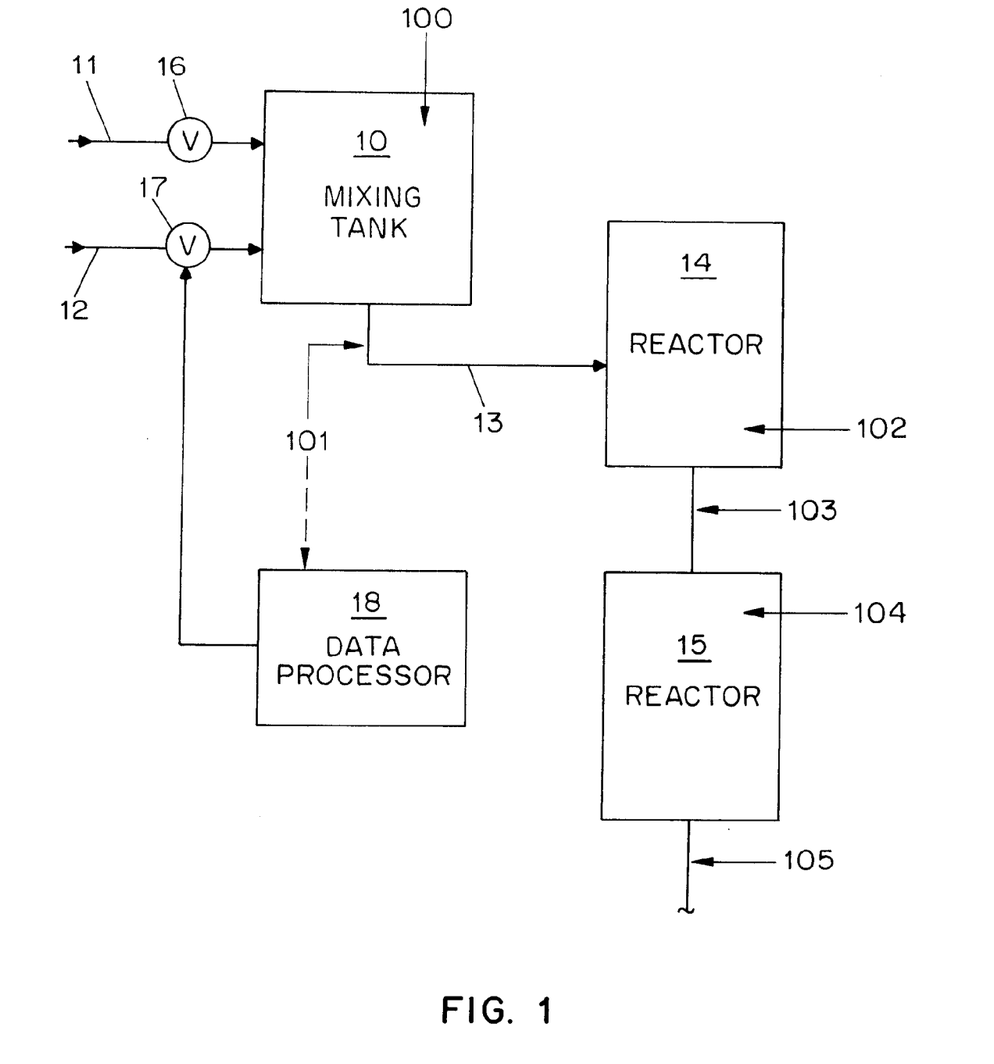
FIG. 1 shows a schematic representation of a basic apparatus which may be used for producing polycarbonate in accordance with the invention.

FIG. 1 shows a schematic representation of a basic apparatus which may be used for producing polycarbonate in accordance with the invention. The apparatus has a monomer mix tank 10 into which streams of dihydric phenol and diaryl carbonate are provided via lines 11 and 12, respectively to form a reaction mixture. The reaction mixture is taken off from the monomer mix tank 10 via line 13 and transported to a first reactor 14 where the first phase of polymerization of the monomers occurs. One or more additional reactors 15 can be included downstream from reactor 14 to finish the polymerization process. Product polycarbonate is recovered from reactor 15 for further processing in accordance with methods known in the art. The apparatus shown in FIG. 1 is configured as a closed system, i.e., a system in which there is no significant loss of volatiles from the system as the polymerization proceeds. For convenience and clarity, this apparatus will be referred to in the following discussion of the method of the invention. It will be appreciated, however, that other apparatus configurations could be employed.

In accordance with a first aspect of the present invention, polycarbonate is made by combining a stream of a dihydric phenol and a stream of diarylcarbonate, and treating this combination with a catalyst to promote oligomerization and/or polymerization. This combined stream of dihydric phenol and diaryl carbonate is referred to herein as the reactant mixture. The reactant mixture has varying composition as it passes first through the monomer mix tank 10 and then through one or more downstream reactors 14, 15. In the method of the present invention, the reaction mixture can be monitored using infrared spectroscopy to evaluate the stoichiometric ratio of dihydric phenol to diarylcarbonate at any convenient point. For example, as illustrated in FIG. 1, monitoring could occur at a point 100 internal to the monomer mix tank, at a point 101 where material leaves the monomer mix tank 10, at a point 102 internal to the first reactor 14, at a point 103 where material leaves the first reactor 14, at a point 104 internal to a second or subsequent reactor 15, or at a point 105 where material leaves the second or subsequent reactor. Monitoring can also be performed on the reaction mixture at more than one location within the apparatus. Monitoring at more than one location may provide an indication that the assumption of a closed system is not valid, and can identify the existence of leaks in the system.

Infrared monitoring in the method of the invention is performed "periodically" during the process and used as a basis for control of the input reagent streams. As used in the specification and claims of this application, the term "periodically" encompasses discrete measurements made at intervals during the process (for example at intervals of 1 to 8 hrs) or more closely spaced measurements, up to an including measurements which, when compared to the duration of the overall process are essentially continuous. For on-line measurements, the measured value determined at any of the sampling points (for example 101 in FIG. 1) is transmitted to a data-processor 18 which interprets the measurement to produce a signal to flow control valves 16 or 17 which control the input rate of the reagents via lines 11 and 12, respectively. The logic applied in interpreting the measured signal is discussed further in the following paragraphs.

In a first embodiment of the invention, the amount of the dihydric phenol in the reaction mixture is monitored periodically to measure the absorbance (peak height or peak area) at one or both of two characteristic peaks, reflecting the methyl CH bonds and hydroxyl OH bonds of the dihydric phenol. In the case of BPA in methylene chloride, suitable absorbance peaks are a CH asymmetric stretch at 2971 cm$^{-1}$ and an OH stretch at 3582 cm$^{-1}$. These peaks may shift in neat samples or in other solvents. In addition, for other dihydric phenols the peak maximum may be shifted somewhat from these numbers, but the corresponding peak would be easily identified by persons skilled in the art. The stream of a dihydric phenol, the stream of diarylcarbonate or both are then adjusted to maintain the overall stoichiometric ratio within a predefined range selected to achieve polycarbonate product with desirable characteristics. As used in the specification and claims of this application, the phrase "overall stoichiometric ratio" refers to the ratio of dihydric phenol moieties, whether as monomers or incorporated into an oligomer, to diaryl carbonate moieties, whether as monomers or incorporated into an oligomer.

Within the monomer mix tank, oligomerization occurs through the addition of a catalyst to create a mixture containing polycarbonate oligomers. The present invention can be used to monitor the overall stoichiometric ratio whether or not a catalyst is added in the monomer mix tank.

Figure 2A:
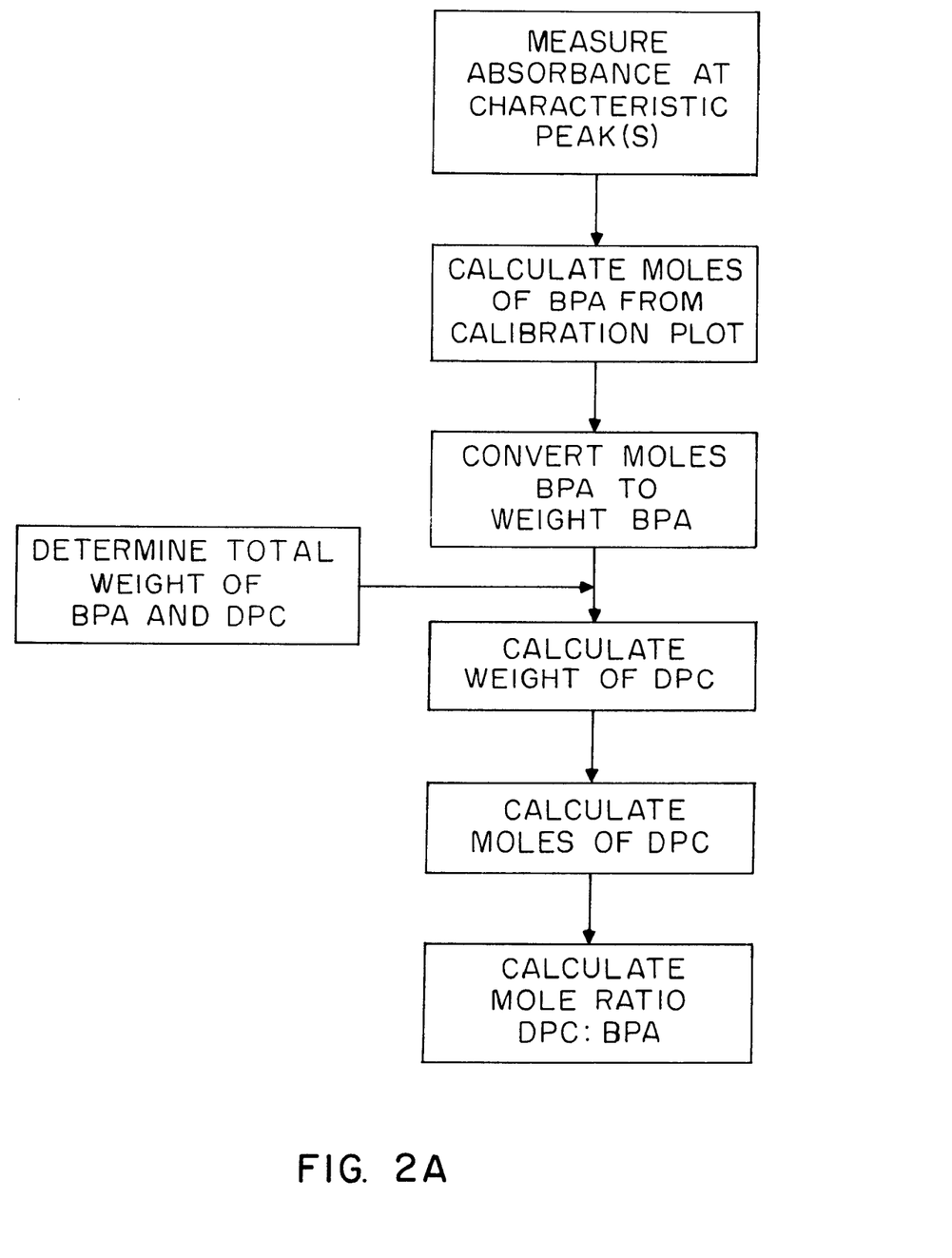
FIGS. 2A and B show an outline of two embodiments of the method of the invention.

A procedure for determining the overall stoichiometric ratio is outlined in FIG. 2A in the context of a BPA/DPC condensation. As shown, a known total weight of BPA+DPC is added to the reaction apparatus. This weight can be determined from the concentration of BPA and DPC in each of the reactant streams and the volume of these streams. At some stage in the process, infrared monitoring is performed to detect a peak associated with BPA. The absorbance is compared to a calibration curve, or interpreted using a calibration constant, to arrive at a concentration of BPA moieties within the monitored reaction mixture. From this concentration, and assuming a closed system containing a known volume of reaction mixture, the number of moles and the weight of BPA in the reaction mixture is determined. The weight of BPA is then subtracted from the known total weight to arrive at the weight of DPC. To determine the stoichiometric ratio, the weight of DPC is converted into moles, and a ratio calculated from the moles of BPA and the moles of DPC.

Figure 2B:
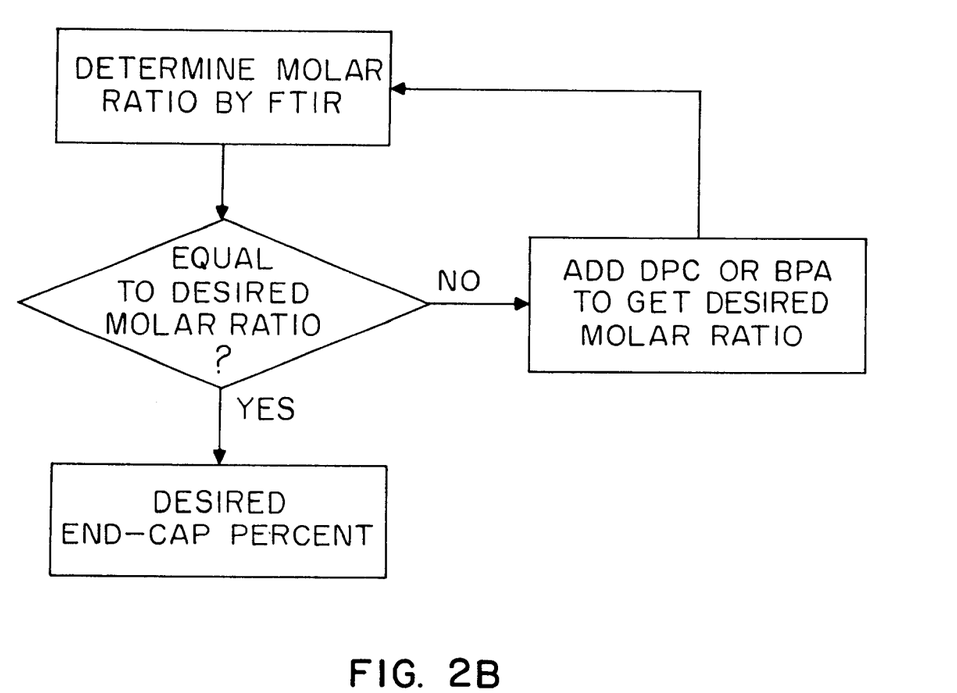

FIG. 2B shows an alternative procedure for determining the overall stoichiometric ratio. In this case, the calibration curve is a plot of the measured absorbance versus the DPC:BPA ratio. As shown, the molar ratio is determined and compared to a predetermined target value. If this comparison indicates that the molar ratio does not meet the target value, DPC or BPA is added to the monomer mix tank as appropriate to achieve the target value. The amount of DPC or BPA to be added is calculated based on the volume of the monomer mix tank. In general, DPC is the component which needs to be added, because it is more volatile.

The method of the present invention can be performed in several variations. In a first embodiment, an aliquot of the material to be assayed is recovered from the system. The amount should be small compared to the total volume of the system unless correction factors are applied. An amount of the recovered material of known weight is made up in a known volume of solvent. The solvent should be free of grossly-interfering bands in the region of the IR spectrum to be measured. A suitable solvent for observation of the OH stretch is dry methylene chloride. Suitable solvents for observation of the CH stretch are o-dichlorobenzene or chloroform. A calibration curve is generated by plotting the peak height (absorbance) as a function of equivalents of OH or CH bonds in the known solution containing a model compound such as DPC or a series of monomer mixes of well-known composition. (See FIGS. 3 and 4). The sample extracted from the polycarbonate production apparatus is analyzed by reading the concentration for the measured peak height from this calibration curve. As shown in Table 2, this method provides excellent correspondence with NMR results on the same samples.

Figure 5:
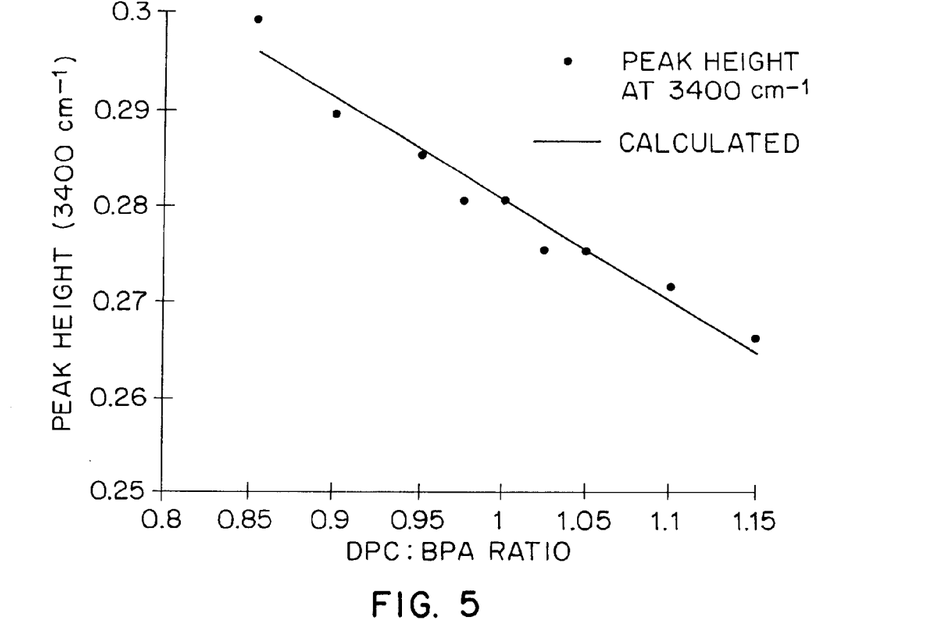
FIG. 5 shows a calibration curve for determination of the equivalents of OH groups using ATR-FTIR methodology.
Figure 6:
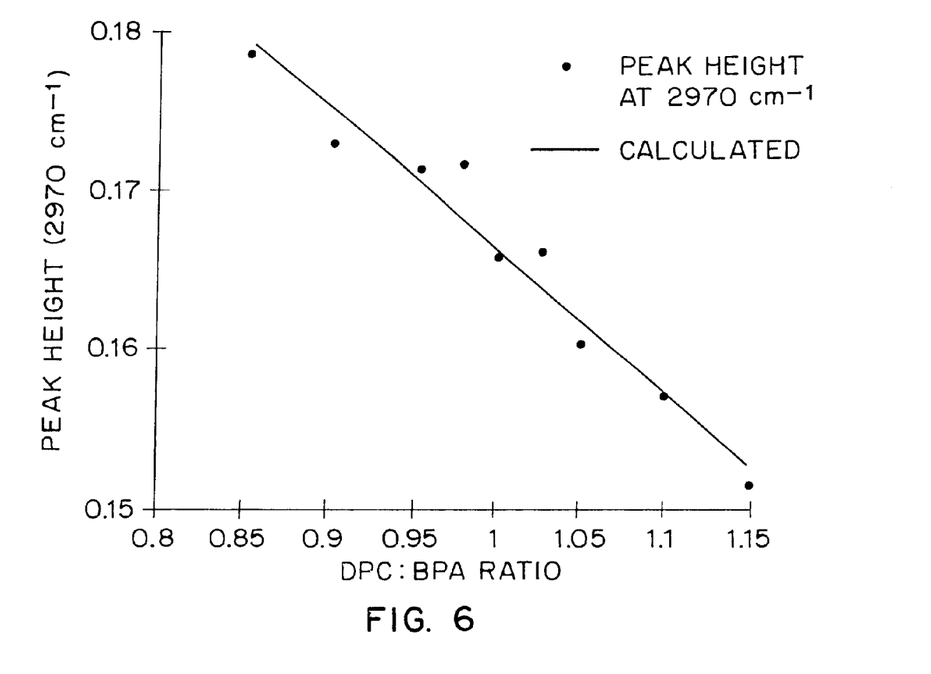
FIG. 6 shows a calibration curve for determination of the equivalents of $CH_3$ groups using ATR-FTIR methodology.

The method of the invention can also be practiced using neat samples of the reaction mixture, an approach which is better suited to in-line measurements. In this case, the preferred methodology is attenuated total reflection fourier transform infrared (ATR-FTIR) spectroscopy using a diamond ATR cell. Calibration curves are generated using a series of standard samples or sample mixtures and can reflect an absorbance associated with either the OH or the CH bonds. (FIGS. 5 and 6)

A third approach for analysis of the infrared data for the samples, which can be practiced using either diluted solution samples or neat samples, relies on the fact that the ratio of carbonyl to methyl groups (reflecting DPC and BPA) remains constant regardless of the degree of polymerization or the amount of phenol which is volatilized during the process of sampling procedure. Thus, the procedure can be used in an open system. In accordance with this embodiment of the invention. a ratio is determined of the size of the carbonyl peak at 1772 $cm^{-1}$ to the methyl peak at 2970 $cm^{-1}$. The determined ratio is compared to a calibration curve such as that shown in FIG. 7 in which the ratios of various standard compositions are plotted as a function of DPC:BPA ratio. This direct measure of the overall stoichiometric ratio can be used to control the addition of DPC or BPA streams to the apparatus.

The invention will now be further described by way of the following non-limiting examples.

Sample Preparation

Procedure A: Equilibrated BPA-DPC mixtures were prepared by charging approximately 45 grams of an appropriate mixture into a 50 mL round bottom flask and heating to 160° C. After the mixture was melted and mixed with a magnetic stirrer, 50 mg of sodium tetraphenyl borate was added as a solid. After 40 minutes (sufficient time to achieve equilibrium), a portion of the sample was poured into an ice-cooled glass vial. Typically, the equilibrated mixtures mixtures solidified as a glass, although samples containing higher BPA:DPC ratios tended to crystallize over several weeks. Using this procedure, less than 1% of generated phenol is lost, as determined by measured in overheads.

Procedure B: To prepare samples with higher molecular weight oligomers, a 1 L glass batch reactor equipped with a solid nickel helical agitator was used. The reactor was charged with solid BPA (0.6570 mol) and solid DPC (0.7096 mol) prior to assembly. The reactor was then assembled, sealed and the atmosphere exchanged with nitrogen three times. The reactor was then brought to near atmospheric pressure with nitrogen and submerged in a fluidized sand bath at 180° C. After 5 minutes, agitation was begun at 250 rpm. After an additional 10 minutes, the reactants were fully melted and a homogenous mixture was assumed. Tetramethyl ammonium hydroxide (0.220 M, $2.5 \times 10^{-4}$ mol/mol BPA) and NaOH ($5 \times 10^{-3}$ M, $1.00 \times 10^{-6}$ mol/mol BPA) were added sequentially. After the final catalyst was added, timing began and the temperature was ramped to 210° C. over five minutes. Once at temperature, the pressure was reduced to 180 mm Hg and phenol distillate was immediately formed. After 25 minutes, the pressure was again reduced to 100 m, Hg and maintained for 45 minutes. After this time, the reactor was brought to 1 atm pressure and the mixture poured onto a metal surface where the oligomeric mixture solidified as a glass.

Experimental IR Analysis

A Nicolet Magna 750 spectrometer was used for FTIR measurements. The instrument was configured with either a DTGS or chilled MCT-B detector using a resolution of 2 or 4 wavenumbers and ranging between 32 and 128 scans before fourier transform. Solution spectra were obtained in the transmission mode using a 0.2 or 0.5 mm KBr cell and a consistent concentration of the process material. ATR spectra were obtained using an ASI multi-bounce diamond ATR liquid sample cell (ASI #071-1001).

Comparative Example

To determine the efficacy of determining overall stoichiometric ratios using HPLC, equilibrated mixtures of known stoichiometry were prepared without removal of phenol using Procedure A. Samples were analyzed by HPLC and the ratio of unreacted DPC:BPA was determined. As shown in Table 1, the for DPC:BPA charging stoichiometries of close to 1 the measured ratio is fairly accurate (±5%), but when the initial charging stoichiometry deviates from 1 the unreacted monemer ratio does not accurately reflect the initial stoichiometry.

TABLE 1

| Sample | Charged Molar Ratio (DPC/BPA) | Measured Ratio by HPLC (Unreacted DPC/BPA) |
| --- | --- | --- |
| 1 | 0.850 | 0.60 |
| 2 | 0.900 | 0.71 |
| 3 | 0.950 | 0.78 |
| 4 | 0.975 | 0.92 |
| 5 | 1.000 | 0.95 |
| 6 | 1.025 | 1.06 |
| 7 | 1.05 | 1.20 |
| 8 | 1.10 | 1.40 |
| 9 | 1.15 | 1.62 |

These results confirm the need for a more robust approach to monitoring the reactant ratios.

EXAMPLE 1

Figure 3:
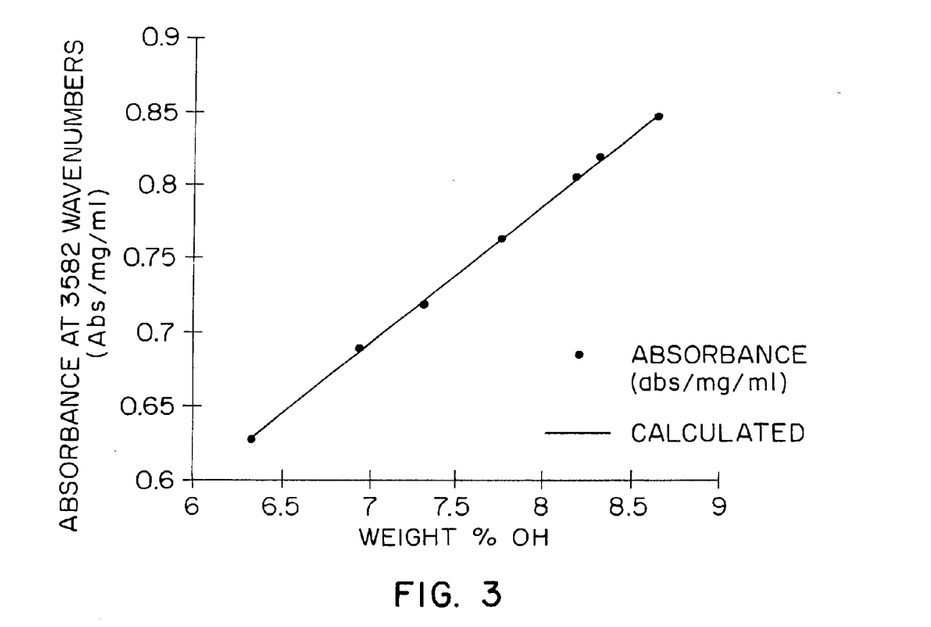
FIG. 3 shows a calibration curve for determination of the equivalents of OH groups using a solution methodology.

To prepare a calibration curve to relate the absorbance of at 3582 $cm^{-1}$ to the amount of BPA in a sample, a series of standard solutions of monomer mixes (BPA+DPC) in methylene chloride were prepared containing known amounts of BPA. Different solutions with different DPC:BPA ratios were prepared. The absorbance at 3582 cm-1 of these solution was measured and plotted as a function of the weight % OH groups. As shown in FIG. 3, this yields a linear calibration curve.

Three model monomer mixes (A, B and C) were prepared by Procedure A with differing DPC:BPA ratios. An oligomer mix was prepared using Procedure B. The weight percent of OH groups in these samples was determined using FTIR spectroscopy and the calibration curve of FIG. 3 and using NMR. As shown in Table 2, there is good correspondence between the two analytical techniques.

TABLE 2

| Sample | FTIR OH conc (wt %) | NMR OH conc (wt %) |
| --- | --- | --- |
| Model Mix A | 7.8 | 7.75 |
| Model Mix B | 8.4 | 8.2 |
| Model Mix C | 7.7 | 7.1 |
| Oligomer | 0.57 | 0.6 |

Replicate runs of model mixes A and B showed that the results using the IR methodology were highly reproducible.

EXAMPLE 3

Figure 4:
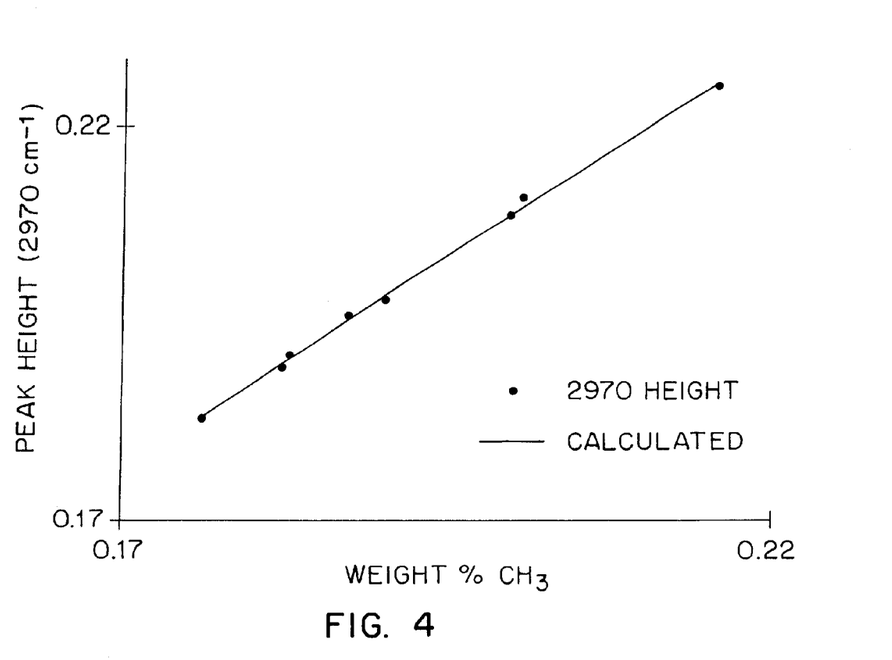
FIG. 4 shows a calibration curve for determination of the equivalents of $CH_3$ groups using a solution methodology.

To prepare a calibration curve to relate the OH absorbance at 3400 $cm^{-1}$ to the amount of BPA in a sample, a series of standard monomer mixes (BPA+DPC) of differing composition were prepared using Procedure A. ATR-FTIR measurements were made, and the peak height at 3400 $cm^{-1}$ was plotted as function of DPC:BPA ratio to yield a calibration curve. As shown in FIG. 4, this yields a linear calibration curve which can be used to determine the stoichiometric ratio of an unknown sample using the procedure outlined in FIG. 2B.

EXAMPLE 4

To prepare a calibration curve to relate the CH stretch absorbance at 2970 $cm^{-1}$ to the amount of BPA in a sample, a series of standard solutions of monomer mixes (BPA+DPC) in o-dichlorobenzene were prepared containing known amounts of BPA. Different solutions with different DPC:BPA ratios were prepared. The absorbance at 2970 $cm^{-1}$ of these solution was measured and plotted as a function of the weight % CH bonds. As shown in FIG. 5, this yields a linear calibration curve.

EXAMPLE 5

To prepare a calibration curve to relate the CH absorbance at 2970 $cm^{-1}$ to the amount of BPA in a sample, a series of standard monomer mixes (BPA+DPC) of differing composition were prepared using Procedure A. ATR-FTIR measurements were made, and the peak height at 2970 $cm^{-1}$ was plotted as function of DPC:BPA ratio to yield a calibration curve. As shown in FIG. 6, this yields a linear calibration curve which can be used to determine the stoichiometric ratio of an unknown sample using the procedure outlined in FIG. 2B.

EXAMPLE 6

Figure 7:
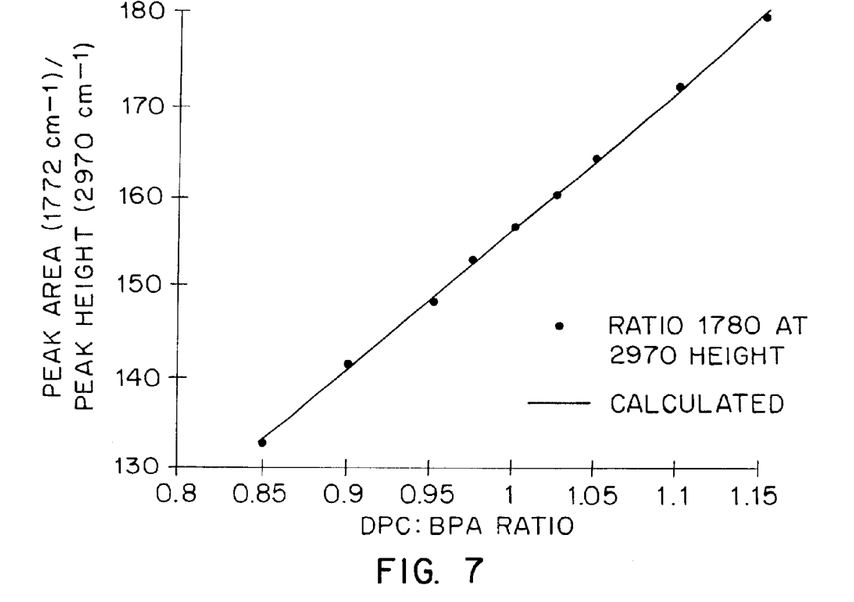
FIG. 7 shows a calibration curve for determination of $CO:CH_3$ by a ratioing methodology in solution.

When a monomer mix is equilibrated, the ratio of carbonyl to methyl (reflecting DPC and BPA, respectively) remains constant regardless of the degree of equilibration or the amount of phenol which is volatilized during the process and regardless of volume changes due to sampling. As a result, there is a proportional relationship between the ratio of peak sizes at 1780 $cm^{-1}$ and 2970 $cm^{-1}$ and the DPC:BPA molar ratio. FIG. 7 shows a calibration curve generated by plotting the ratio of the area of the carbonyl peak (1772 $cm^{-1}$) to the height of the methyl peak (2970 $cm^{-1}$) as a function of DPC:BPA ratio in monomer mixes with minimum phenol losses. The linear calibration curve was generated using monomer mixes prepared by Procedure A in o-dichlorobenzene. The curve could also be a plot of area:area or height:height or height:area as a function of DPC:BPA ratio.

EXAMPLE 7

The carbonyl/methyl ratio methodology of Example 6 was used to evaluate samples taken from Reactors 1 and 2 of an operating polycarbonate plant on different days. Theoretical stoichiometric ratios were determined based on flow rates in and out of the reactors. The samples were diluted (2 g/100 ml) in o-dichlorobenzene and analyzed by FTIR. The area to height ratio (A/H) was calculated and used to determine the DPC:BPA ratio. The results are summarized in Table 3. As shown, the FTIR results are in close conformity with the theoretical ratio.

TABLE 3

| Source | CO peak area | $CH_3$ peak height | A/H Ratio | Theor Ratio | FTIR ratio |
| --- | --- | --- | --- | --- | --- |
| Reactor 1 | 23.661 | 0.149 | 158.8 | 1.083 | 1.091 |
| Reactor 1 | 23.654 | 0.151 | 157.0 | 1.080 | 1.078 |
| Reactor 1 | 23.632 | 0.148 | 159.4 | 1.085 | 1.095 |
| Reactor 1 | 23.515 | 0.145 | 158.8 | 1.089 | 1.091 |
| Reactor 1 | 23.012 | 0.145 | 158.4 | 1.094 | 1.088 |
| Reactor 2 | 26.405 | 0.174 | 151.4 | 1.044 | 1.040 |
| Reactor 2 | 25.545 | 0.170 | 150.5 | 1.060 | 1.034 |
| Reactor 2 | 26.503 | 0.172 | 151.1 | 1.042 | 1.038 |

EXAMPLE 8

Figure 8:
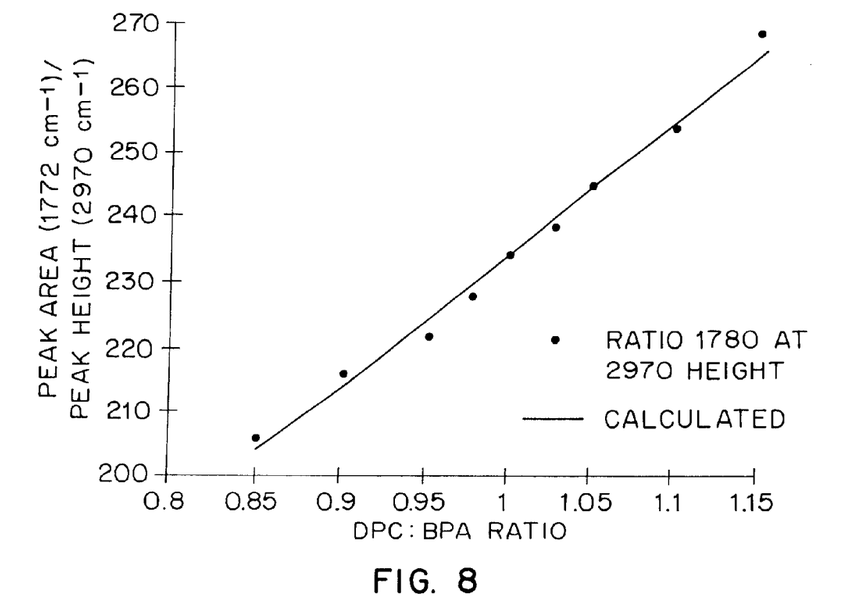
FIG. 8 shows a calibration curve for determination of $CO:CH_3$ by a ratioing methodology by ATR-FTIR.

FIG. 8 shows a calibration curve generated using the carbonyl-methyl ratio method and ATR-FTIR measurements on neat samples of equilibrated monomer mixes prepared using procedure A.

What is claimed is:

1. A method for making polycarbonate, comprising the steps of:
   (a) combining a stream of a dihydric phenol and a stream of diarylcarbonate to form a reaction mixture;
   (b) passing the reaction mixture through a series of reaction stages in which the dihydric phenol and the diarylcarbonate react to form polycarbonate; and
   (c) periodically monitoring the composition of the reaction mixture at one or more of the reaction stages to determine the overall stoichiometric ratio of dihydric phenol to diarylcarbonate; and
   (d) adjusting the stream of a dihydric phenol, the stream of diarylcarbonate or both to maintain the overall stoichiometric ratio within a predefined range,
   wherein the composition of the reaction mixture is monitored using infrared spectroscopy.

2. The method of claim 1, wherein the reaction stages include a monomer mix tank and one or more reactors disposed downstream from the monomer mix tank.

3. The method of claim 2, wherein the composition of the reaction mixture is monitored in the monomer mix tank.

4. The method of claim 1, wherein the composition of the reaction mixture is monitored using a Fourier Transform Infrared Spectrometer.

5. The method of claim 1, wherein the composition of the reaction mixture is monitored using infrared spectroscopy to determine an absorbance of a peak associated with the OH stretch of the dihydric phenol, and further comprising the steps of determining a calculated weight of dihydric phenol in the reaction mixture based on the absorbance of the peak associated with the OH stretch, subtracting the calculated weight of dihydric phenol from a known total weight of dihydric phenol plus diarylcarbonate to arrive at a calculated weight of diaryl carbonate in the reaction mixture, and determining the overall stoichiometric ratio as a molar ratio of diarylcarbonate to dihydric phenol from the calculated weights of diarylcarbonate and dihydric phenol.

6. The method of claim 5, wherein the calculated weight of dihydric phenol is determined by comparing the absorbance of the peak associated with the OH stretch with a calibration curve.

7. The method of claim 1, wherein the composition of the reaction mixture is monitored using infrared spectroscopy to determine an absorbance of a peak associated with the CH stretch of the dihydric phenol, and further comprising the steps of determining a calculated weight of dihydric phenol in the reaction mixture based on the absorbance of the peak associated with the CH stretch, subtracting the calculated weight of dihydric phenol from a known total weight of dihydric phenol plus diarylcarbonate to arrive at a calculated weight of diaryl carbonate in the reaction mixture, and determining the overall stoichiometric ratio as a molar ratio of diarylcarbonate to dihydric phenol from the calculated weights of diarylcarbonate and dihydric phenol.

8. The method of claim 7, wherein the calculated weight of dihydric phenol is determined by comparing the absorbance of the peak associated with the CH stretch with a calibration curve.

9. The method of claim 1, wherein the composition of the reaction mixture is monitored using infrared spectroscopy to determine a measure of the size of a peak associated with the carbonyl stretch of the diarylcarbonate, and a measure of the size of a peak associated with the CH stretch of the dihydric phenol, and wherein the overall stoichiometric ratio as a molar ratio of diarylcarbonate to dihydric phenol from the calculated weights of diarylcarbonate and dihydric phenol is determined.

10. An apparatus for production of polycarbonate, comprising
(a) a source for a reagent streams of dihydric phenol;
(b) a source for a reagent streams of diarylcarbonate;
(c) a mix tank, connected to the sources for reagent streams of dihydric phenol and diarylcarbonate, said streams being mixed in the mix tank to form a reaction mixture;
(d) at least one control valve disposed to control introduction of the reagent stream of dihydric phenol or diaryl carbonate into the mix tank;
(e) one or more reactors connected to the mix tank to receive the reaction mixture formed therein, said one or more reactors further containing a catalyst for catalyzing the formation of polycarbonate from the dihydric phenol and the diarylcarbonate; and
(f) an infrared spectrometer disposed to measure the absorbance of the reaction mixture at one or more characteristic absorption wavelengths associated with the dihydric phenol or the diarylcarbonate; and
(g) a processor operatively connected to the spectrometer for receiving an indication of the absorbance of the reaction mixture, said processor deriving a flow-rate signal from the indication of the absorbance and transmitting the flow rate signal to the control valve.

11. The apparatus of claim 10, wherein the infrared spectrometer is a fourier transform infrared spectrometer.

12. The apparatus of claim 10, wherein the infrared spectrometer is disposed to measure the absorbance of the reaction mixture in the mix tank.

13. The apparatus of claim 10, wherein the infrared spectrometer is a fourier transform infrared spectrometer.

14. The apparatus of claim 10, wherein the infrared spectrometer is disposed to measure the absorbance of the reaction mixture at a plurality of locations.

15. A method for controlling the end-cap level in a polycarbonate resin produced by reaction of a dihydric phenol and diarylcarbonate, comprising the steps of:
(a) measuring the absorbance of a reaction mixture formed from the dihydric phenol and the diarylcarbonate at one or more characteristic absorption wavelengths associated with the dihydric phenol or the diarylcarbonate; and
(b) converting the measured absorbance into an overall stoichiometric ratio of dihydric phenol to diaryl carbonate in the reaction mixture; and
(c) adjusting the amount of dihydric phenol or diaryl carbonate in the reaction mixture to change the overall stoichiometric ratio to a desired level.

16. The method of claim 15, wherein the composition of the reaction mixture is monitored using infrared spectroscopy to determine an absorbance of a peak associated with the OH stretch of the dihydric phenol, and further comprising the steps of determining a calculated weight of dihydric phenol in the reaction mixture based on the absorbance of the peak associated with the OH stretch, subtracting the calculated weight of dihydric phenol from a known total weight of dihydric phenol plus diarylcarbonate to arrive at a calculated weight of diaryl carbonate in the reaction mixture, and determining the overall stoichiometric ratio as a molar ratio of diarylcarbonate to dihydric phenol from the calculated weights of diarylcarbonate and dihydric phenol.

17. The method of claim 16, wherein the calculated weight of dihydric phenol is determined by comparing the absorbance of the peak associated with the OH stretch with a calibration curve.

18. The method of claim 15, wherein the composition of the reaction mixture is monitored using infrared spectroscopy to determine an absorbance of a peak associated with the CH stretch of the dihydric phenol, and further comprising the steps of determining a calculated weight of dihydric phenol in the reaction mixture based on the absorbance of the peak associated with the CH stretch, subtracting the calculated weight of dihydric phenol from a known total weight of dihydric phenol plus diarylcarbonate to arrive at a calculated weight of diaryl carbonate in the reaction mixture, and determining the overall stoichiometric ratio as a molar ratio of diarylcarbonate to dihydric phenol from the calculated weights of diarylcarbonate and dihydric phenol.

19. The method of claim 18, wherein the calculated weight of dihydric phenol is determined by comparing the absorbance of the peak associated with the CH stretch with a calibration curve.

20. The method of claim 15, wherein the composition of the reaction mixture is monitored using infrared spectroscopy to determine a measure of the size of a peak associated with the carbonyl stretch of the diarylcarbonate, and a measure of the size of a peak associated with the CH stretch of the dihydric phenol, and wherein the overall stoichiometric ratio as a molar ratio of diarylcarbonate to dihydric phenol from the calculated weights of diarylcarbonate and dihydric phenol is determined.

* * * * *